(12) United States Patent
Furst et al.

(10) Patent No.: US 10,275,576 B2
(45) Date of Patent: Apr. 30, 2019

(54) AUTOMATIC MEDICAL CODING SYSTEM AND METHOD

(71) Applicant: Passport Health Communications, Inc., Franklin, TN (US)

(72) Inventors: Elizabeth Furst, Nolensville, TN (US); Jennifer Lynn Swindell, Nolensville, TN (US)

(73) Assignee: PASSPORT HEALTH COMMUNICATIONS, INC, Franklin, TN (US)

( * ) Notice: Subject to any disclaimer, the term of this patent is extended or adjusted under 35 U.S.C. 154(b) by 785 days.

(21) Appl. No.: 14/727,474

(22) Filed: Jun. 1, 2015

(65) Prior Publication Data
US 2015/0379241 A1 Dec. 31, 2015

Related U.S. Application Data

(60) Provisional application No. 62/018,423, filed on Jun. 27, 2014.

(51) Int. Cl.
 *G06F 19/00* (2018.01)
 *G16H 10/60* (2018.01)
 *G06F 17/27* (2006.01)

(52) U.S. Cl.
 CPC ............ *G06F 19/36* (2013.01); *G06F 17/273* (2013.01); *G06F 17/2705* (2013.01); *G06F 17/2795* (2013.01); *G06F 19/328* (2013.01); *G16H 10/60* (2018.01)

(58) Field of Classification Search
 CPC ...... G06F 19/36; G06F 19/328; G06F 17/273; G06F 17/2705; G06F 17/2795; G16H 10/60
 See application file for complete search history.

(56) References Cited

U.S. PATENT DOCUMENTS

| | | | |
|---|---|---|---|
| 2003/0069760 A1* | 4/2003 | Gelber | G06Q 40/02 705/4 |
| 2006/0026003 A1* | 2/2006 | Carus | G10L 15/01 704/275 |
| 2007/0226211 A1* | 9/2007 | Heinze | G06F 17/30011 |
| 2010/0010989 A1* | 1/2010 | Li | G06F 17/273 707/E17.017 |
| 2011/0040576 A1* | 2/2011 | Madan | G06Q 10/10 705/3 |
| 2012/0278102 A1* | 11/2012 | Johnson | G06Q 10/10 705/3 |

* cited by examiner

*Primary Examiner* — Eliza A Lam
(74) *Attorney, Agent, or Firm* — Merchant & Gould (57) ABSTRACT

An automatic medical coding system is provided. The system parses features of natural language diagnosis and procedure information. The features are compared to elements of a medical coding system. Medical codes corresponding to medical coding system elements that match features of the diagnosis and procedure information are mapped to the received diagnosis and procedure information. The mapped medical code is assigned a score reflecting the estimated reliability of the mapped medical code based on the amount of manipulation of the received diagnosis and procedure information leading to the match. The scored medical code may be submitted to a workflow making use of medical codes. The scored medical code may optionally be presented to a user for review prior to further utilization of the scored medical code.

20 Claims, 3 Drawing Sheets

AUTOMATIC MEDICAL CODING SYSTEM AND METHOD

CROSS REFERENCE TO RELATED APPLICATION

This application claims the benefit of U.S. Provisional Application No. 62/018,423, titled "Automatic Medical Coding System and Method" filed Jun. 27, 2014.

BACKGROUND

Medical coding is the process of assigning a code that uniquely identifies a diagnosis or procedure. Proper medical coding is almost always required before a request for reimbursement (e.g., an insurance claim) will be approved by a payer (e.g., a health insurance company). There are often pre-claim documents that must be submitted in order to support a request for reimbursement and require proper medical coding before being accepted by the payer. Examples of such pre-claim documents are notices of admission, prior authorization requests for health care services, referrals, and the like. Additionally, proper medical coding may provide more complete or accurate information in other applications, such as medical necessity inquiries.

Medical coding is usually manually performed by specialized personnel having a significant amount of training, education, experience, and knowledge of the various medical coding systems used and payer requirements. Medical coders review medical records and select appropriate medical codes from medical coding systems. In many cases, medical coding does not occur until after a patient encounter ends (i.e., after the patient checks out) when a request for reimbursement is being prepared for submission to a payer. While skilled at what they do, other health care workers (e.g., admissions and scheduling personnel), are not normally expected, nor required, to be proficient medical coders.

Accordingly, medical coding information is not routinely available when pre-claim communications with the payer should occur, such as when admitting patients, scheduling future appointments/procedures, making referrals, and other activities. For example, the person scheduling a future procedure is more likely than not selecting a visit type (i.e., procedure), such as "MRI of the chest," without selecting a specific code from a medical coding system required for a request for reimbursement or supporting pre-claim documents. The diagnosis is typically recorded as a narrative (i.e., free text) description in a note field. The phrasing of the narrative description may vary wildly. For example, abdominal pain might be described using "stomach pain," "belly ache," "gastroenteritis," or other phrases, depending upon who is involved in providing and entering the information. It is not until later when the medical coder sorts out the description that the necessary documentation can be submitted to the payer. The separation between the activity necessitating filing of documentation with a payer and having the medical coding needed to file the documentation introduces delay and opportunities for errors to occur that may result in the health care provider not being reimbursed. It is with respect to these and other considerations that the present disclosure has been made.

BRIEF SUMMARY

Various aspects of an automatic medical coding system include a parser, a mapper, and an optional scorer. In operation, the automatic medical coding system receives messages containing diagnosis or procedure information and maps that information to one or more medical codes. The diagnosis or procedure information may be a natural language description of a diagnosis or procedure. The parser collects features of the diagnosis or procedure information. The features are extracted or derived from the diagnosis or procedure information for evaluation when attempting to map the diagnosis or procedure information to a medical code.

The automatic medical coding system may optionally include databases, such as a medical terminology database, linking terminology appearing in a medical coding system with synonyms, lay terminology, abbreviations, and/or acronyms and a spelling dictionary. The parser may manipulate the diagnosis or procedure information based on the contents of the databases. For example, synonyms may be substituted and abbreviations may be expanded to normalize the diagnosis or procedure information, unsupervised spelling corrections may be made, and punctuation and other semantic signals may be used to distinguish between several separate diagnoses or procedures appearing the diagnosis or procedure information. The manipulated information may optionally be parsed into features. The parser may apply the semantic rules to manipulate the diagnosis or procedure information. For example, punctuation may be used to distinguish multiple diagnoses or procedures, or conjunctions may be used to relate a procedure to multiple diagnoses. The manipulated information may then be parsed into features. The manipulations are not mutually exclusive and may be mixed and matched as appropriate to generate information manipulated in different ways to produce a variety of features for use in the mapping process.

The mapper may accept the diagnosis or procedure information, or portions thereof, as received and as manipulated by the parser as inputs, or the mapper may accept the features collected by the parser as inputs. The mapper evaluates the inputs of the diagnosis or procedure information against elements of a medical coding system database. The medical coding system database contains information pertaining to one or more medical coding systems. The medical coding system database may include, without limitation, a set of medical codes and associated medical code descriptions. Each medical code description specifies a diagnosis or procedure corresponding to each medical code. In aspects of the automatic medical coding system, the mapper compares the features to the medical code descriptions. When a match is found, the medical code corresponding to the matching element of the medical coding system database is mapped with the diagnosis or procedure information. Mapped medical codes may include a score (e.g., a confidence value) assigned by the mapper. An optional scorer may evaluate the scores associated with the mapped medical codes and rank the matches to determine the best result.

BRIEF DESCRIPTION OF THE DRAWINGS

Further features, aspects, and advantages of the disclosure represented by the embodiments described in the present disclosure will become better understood by reference to the following detailed description, appended claims, and accompanying Figures, wherein elements are not to scale so as to more clearly show the details, wherein like reference numbers indicate like elements throughout the several views, and wherein:

DETAILED DESCRIPTION

An automatic medical coding system is described herein and illustrated in the accompanying figures. The system parses features of natural language diagnosis and procedure information. The features are compared to elements of a medical coding system. Medical codes corresponding to medical coding system elements that match features of the diagnosis and procedure information are mapped to the received diagnosis and procedure information. The mapped medical code is assigned a score reflecting the estimated reliability of the mapped medical code based on the amount of manipulation of the received diagnosis and procedure information leading to the match. The scored medical code may be submitted to a workflow making use of medical codes. The scored medical code may optionally be presented to a user for review prior to further utilization of the scored medical code.

As used herein, a medical coding system refers to a classification, coding, or nomenclature system for medical diagnoses and/or procedures. A medical coding system typically includes a set of medical codes and associated medical code descriptions. Each medical code description corresponds to a medical code and describes the diagnoses and/or procedures covered under the code. Examples of widely recognized medical coding systems include, but are not limited to, the International Classification of Diseases, Clinical Modification (e.g., ICD-9-CM and ICD-10-CM), the Current Procedural Terminology (CPT®) system, and the Code on Dental Procedures and Nomenclature (CDT). Medical codes are almost always required when submitting claims and pre-claim documentation for reimbursement to a payer, and are regularly used in monitoring and reporting of diseases.

Figure 1:
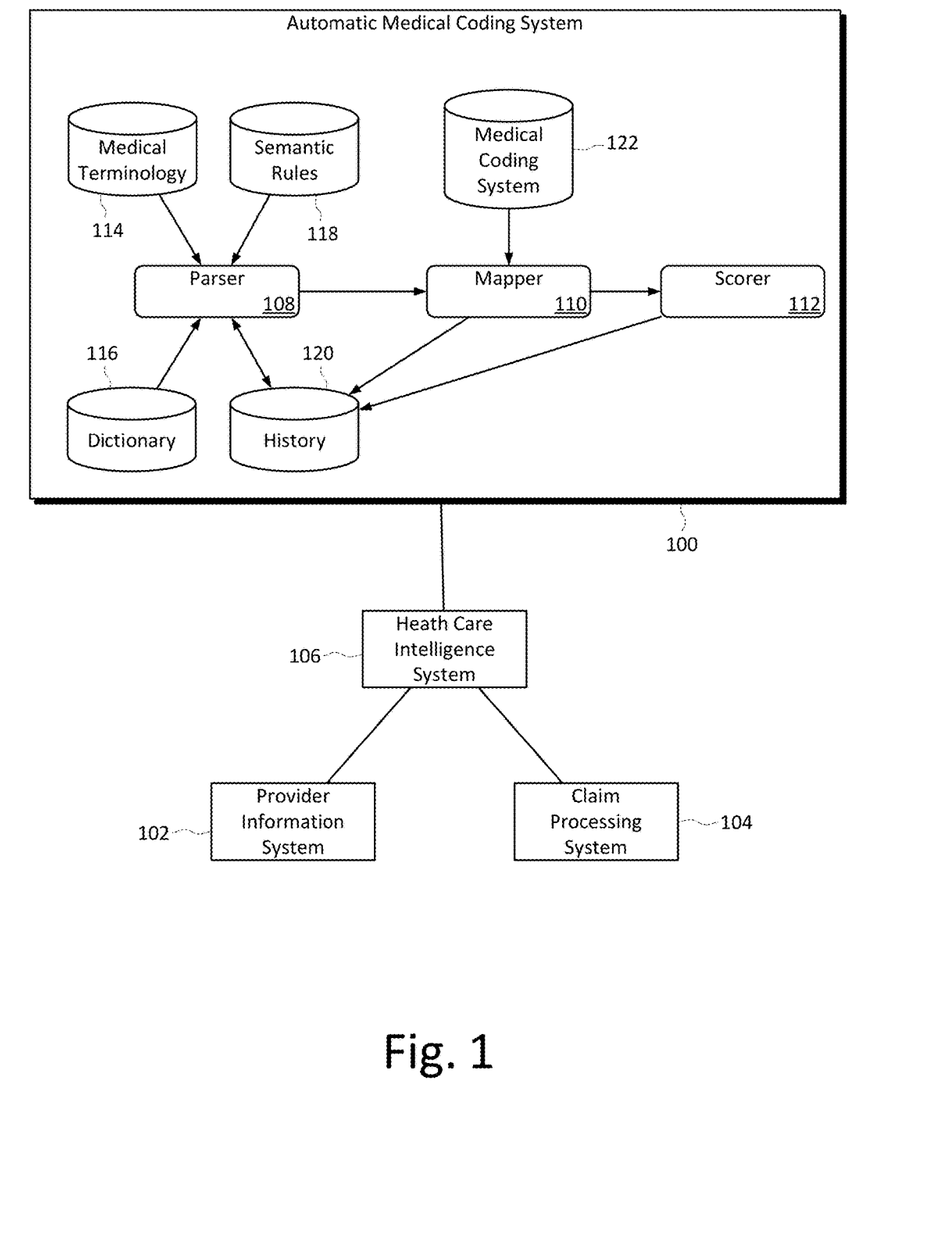
FIG. 1 illustrates one embodiment of the automatic medical coding system in a suitable operating environment.

FIG. 1 illustrates one embodiment of an automatic medical coding system 100 in a suitable operating environment. The automatic medical coding system 100 provides automatic translations of natural language diagnosis or procedure descriptions into medical codes used to uniquely identify a diagnosis or procedure. The automatic medical coding system 100 may be in communication with a provider information system 102 maintained and operated by a health care provider (e.g., a doctor office, a dentist office, or hospital) to automatically add medical codes to patient records based on diagnosis or treatment notes documenting a patient encounter. In another example, the automatic medical coding system 100 may be in communication with a claim processing system 104 maintained and operated by a payer (e.g., a health insurance company, a government entity, or an employer) to add medical codes to documents submitted without medical codes by a health care provider. In yet another example, the automatic medical coding system 100 may be in communication with a health care intelligence system 106 maintained and operated by a health care intelligence vendor allowing the health care intelligence vendor to provide automatic medical coding services to health care providers, payers, or other entities.

The provider information system 102 may store business and patient information used by the health care provider, such as insurance information, electronic medical records, billing information, and appointments. The claim processing system 104 provides information about insurance coverage and eligibility, and handles the reimbursement of claims. The health care intelligence system 106 may be used to provide intelligence services, such as data collection, data verification, and pre-submission document validation. The health care intelligence system 106 may also serve as an interface between health care providers and payers to normalize communication solutions, data requirements, and transaction formats.

The automatic medical coding system 100, the provider information system 102, the claim processing system 104, the health care intelligence system 106, and any associated systems may be implemented using one or more computing devices executing corresponding computer executable instructions that provide the functionality described herein. The computer executable instructions may be in the form of programs, applications, services, scripts, or other software. The computing devices may be implemented in various configurations, such as, without limitation, individual servers or server farms. A server or other computing device may assume a single role or multiple roles. For example, a computing device may serve as a dedicated automatic medical coding system 100 (i.e., a single role) or provide automatic medical coding functionality and health care intelligence functionality (i.e., multiple roles). In a distributed environment, the distributed systems communicate via one or more networks, such as, but not limited to, the Internet, wide area networks, and local area networks.

The automatic medical coding system 100, the provider information system 102, the claim processing system 104, and the health care intelligence system 106 may use a combination of electronic data interchange (EDI) transactions, web services, web forms, and web pages to interactively communicate with other systems. Communications (i.e., messages) between the various systems are encrypted or otherwise secured at or above the level required to comply with applicable health care information privacy laws, regulations, and standards.

In operation, the automatic medical coding system 100 receives messages containing diagnosis or procedure information and maps that information to one or more medical codes. The diagnosis or procedure information may be a natural language description of a diagnosis or procedure. Examples of natural language descriptions include, without limitation, narrative descriptions of a patient encounter (e.g., health care provider notes) and selections from pre-defined lists of diagnoses or procedures. Typically, the diagnosis or procedure information contains no readily identifiable medical code; however, in some instances, the diagnosis or procedure information may contain a full medical code or a partial medical code.

According to aspects, the automatic medical coding system 100 may include a parser 108, a mapper 110, and an optional scorer 112. When a message is received, the automatic medical coding system 100 identifies and extracts the portion or portions of the message potentially containing diagnosis or procedure information, and passes the extracted information to the parser 108. Depending upon the various factors, such as the system generating the message, the type of message, and user preferences, the diagnosis or procedure information may appear in different places (i.e., fields). Examples of fields potentially containing diagnosis or procedure information including patient complaint fields, physician notes fields, and visit type fields. Some messages, for example, may contain fields that are unrelated to diagnoses or procedures (e.g., demographic or financial data). In such cases, the automatic medical coding system 100 only selected fields likely to contain the diagnosis or procedure information are extracted and passed to the parser 108. In some instances, the message received at the automatic medical coding system 100 may contain only the diagnosis or procedure information to be processed (e.g., a narrative description sent specifically for medical code mapping or pre-processed by another system) so the entire message is passed to the parser 108.

The parser 108 may apply algorithms, rules, logic, or statistical models to search the extracted data for diagnosis or procedure information and map that information to one or more medical coding systems based on features of the diagnosis or procedure information. Examples of features include, but are not limited to, alphanumeric sequences, words, and phrases (e.g., word n-grams) appearing in the diagnosis or procedure information. Features may also be derived by applying one or more manipulations to the diagnosis or procedure information. The extracted information may contain multiple instances of diagnosis or procedure information that may be identified by the parser 108.

The automatic medical coding system 100 may optionally include a medical terminology database 114 linking terminology appearing in a medical coding system with synonyms, lay terminology, abbreviations, and/or acronyms. The parser 108 may manipulate the diagnosis or procedure information based on the contents of the medical terminology database 114. For example, synonyms may be substituted and abbreviations may be expanded to normalize the diagnosis or procedure information. The manipulated information may then be parsed into features.

The automatic medical coding system 100 may optionally include a spelling dictionary 116 that may be used by the parser 108 for making unsupervised spelling corrections to the diagnosis or procedure information. The manipulated information may then be parsed into features.

The automatic medical coding system 100 may optionally include semantic rules 118 for rearranging or separating the diagnosis or procedure information based on semantic signals, such as grammar and parts-of-speech. The parser 108 may apply the semantic rules 118 to manipulate the diagnosis or procedure information. For example, punctuation may be used to distinguish between several separate diagnoses or procedures appearing the diagnosis or procedure information, or conjunctions may be used to relate a procedure to multiple diagnoses. The manipulated information may then be parsed into features.

An optional history database 120 may be used to store historical information about the medical codes that are automatically mapped in general or to a particular string or set of words from the diagnosis or procedure information. The history database 120 may include data specific to a particular entity (e.g., a particular health care provider) and/or data of general applicability from multiple entities. The data in the history database 120 may specifically be collected by the automatic medical coding system 100 or be obtained or derived from data collected by a third party. The history data may be used as a factor in determining the probability that an automatically mapped medical code is the most correct medical code for a narrative description of a diagnosis or procedure sent to the automatic medical coding system 100 for processing.

While described as separate databases, one or more of the databases may be consolidated in a single database. For example, the spelling dictionary 116 may be integrated with the terminology database 114.

The manipulations described herein are not mutually exclusive and may be mixed and matched as appropriate to generate information manipulated in different ways to produce a variety of features for use in the mapping process. For example, the spell-corrected information may be used to build any of the features described herein. Another set of features may be built using information that has been spell-corrected and subjected to normalization manipulations. Still more features may be built from rearrangements of spell-corrected information, rearrangements of normalized information, and rearrangements of spell-corrected and normalized information.

The features collected by the parser 108 serve as the inputs to the mapper 110. The features may have one or more associated scores (e.g., confidence values). The scores may be based on the amount of manipulation used to produce the feature. The scores may be a single composite score accounting for all manipulations or individual scores for each manipulation.

The mapper 110 evaluates the features of the diagnosis or procedure information against elements of a medical coding system database 122. The medical coding system database 122 contains information pertaining to one or more medical coding systems. The medical coding system database 122 may include, without limitation, a set of medical codes and associated medical code descriptions. Each medical code description specifies a diagnosis or procedure corresponding to each medical code. The medical coding system database 122 may also provide a cross-reference for mapping a medical code in one medical coding system to other medical coding systems.

To provide a frame of reference, ICD-9-CM codes are three to five digits. The first digit is either numeric or alphabetic (the letters E or V only) and all other digits are numeric. The first three digits specify the category. The final one or two digits specify a etiology (causation), anatomic site, and/or manifestation and are separated from the first three digits by a period. ICD-10-CM codes are up to seven digits. The first digit is always alphabetic (any letter except U), the second digit is always numeric, and the remaining five digits are alphanumeric. The first three digits specify the category. The next one to four digits specify an etiology, anatomic site, or severity and are separated from the first three digits by a period. The final digit is an extension used to supply additional information (e.g., obstetric information, injuries, external causes of injury, complications, etc.). CPT® codes are five digits with the first four digits being numeric and the final digit being numeric or alphabetic (only F or T).

In claim documentation, CPT® codes focus on the services rendered (i.e., procedure or treatment) while ICD codes primarily focus on diagnosis. Consider an example of the diagnosis and treatment for chronic arthritis in the left shoulder caused by kidney failure with no masses of uric acid crystals. The ICD-9-CM code would be 274.02 with a corresponding description of "chronic gouty arthropathy without mention of tophus (tophi)", the ICD-10-CM code would be M1A.3120 with a corresponding description of "chronic gout due to renal impairment, left shoulder, without tophus (tophi)", and the corresponding CPT® code might be 20610 with a corresponding description of "arthrocentesis, aspiration and/or injection; major joint or bursa (e.g., shoulder, hip, knee joint, subacromial bursa)."

In embodiments of the automatic medical coding system 100, the mapper 110 compares the features to the medical code descriptions. When a match is found, the medical code corresponding the matching element of the medical coding system database 122 is mapped with the diagnosis or procedure information. The mapper 110 may make the comparisons using a wide variety of techniques including, without limitation, hand crafted rules, decision trees, and statistical models. The mapper 110 may search via exact matching and fuzzy matching techniques. In various embodiments, the mapper 110 may identify more than one medical code potentially corresponding to the diagnosis or procedure information. In some instances, multiple medical codes may be the result of multiple diagnoses and/or procedures appearing in the diagnosis or procedure information. In other instances, multiple medical codes may be the result of competing matches for a single diagnosis and/or procedure. Mapped medical codes may include a score (e.g., a confidence value) assigned by the mapper 110. The score may be influenced by a variety of factors including, but not limited to, the number of matching medical codes mapped to the diagnosis and procedure information.

The optional scorer 112 evaluates the scores associated with the mapped medical codes. If multiple medical codes are mapped to information describing a single diagnosis and/or procedure, the scorer 112 may rank the matches. The scorer 112 may return a selected number of mapped medical codes that have been mapped to the diagnosis or procedure information. For example, the scorer 112 may return a single mapped medical code (e.g., the one best or top result) or a ranked list of mapped medical codes (e.g., an n-best list).

The medical codes may be used to process a workflow (e.g., generate/complete and submit a pre-authorization request, a medical necessity inquiry, or a notice of admission), update the provider information system 102, or for other purposes. The automatically mapped medical codes may optionally be sent to the provider information system 102 where they are presented to the user, together with information used to determine the medical codes, for approval. In various embodiments, approval may be required before the medical codes are used.

In the illustrated embodiment, the automatic medical coding system 100 appears as an independent system operating in conjunction with the health care intelligence system 106, which serves as a front end. However, any of the provider information system 102, the claim processing system 104, and the health care intelligence system 106 may be configured to interact with the automatic medical coding system 100 to automatically obtain medical codes. Further, the automatic medical coding system 100 may be integrated into another system, including any of those described herein.

Figure 2:
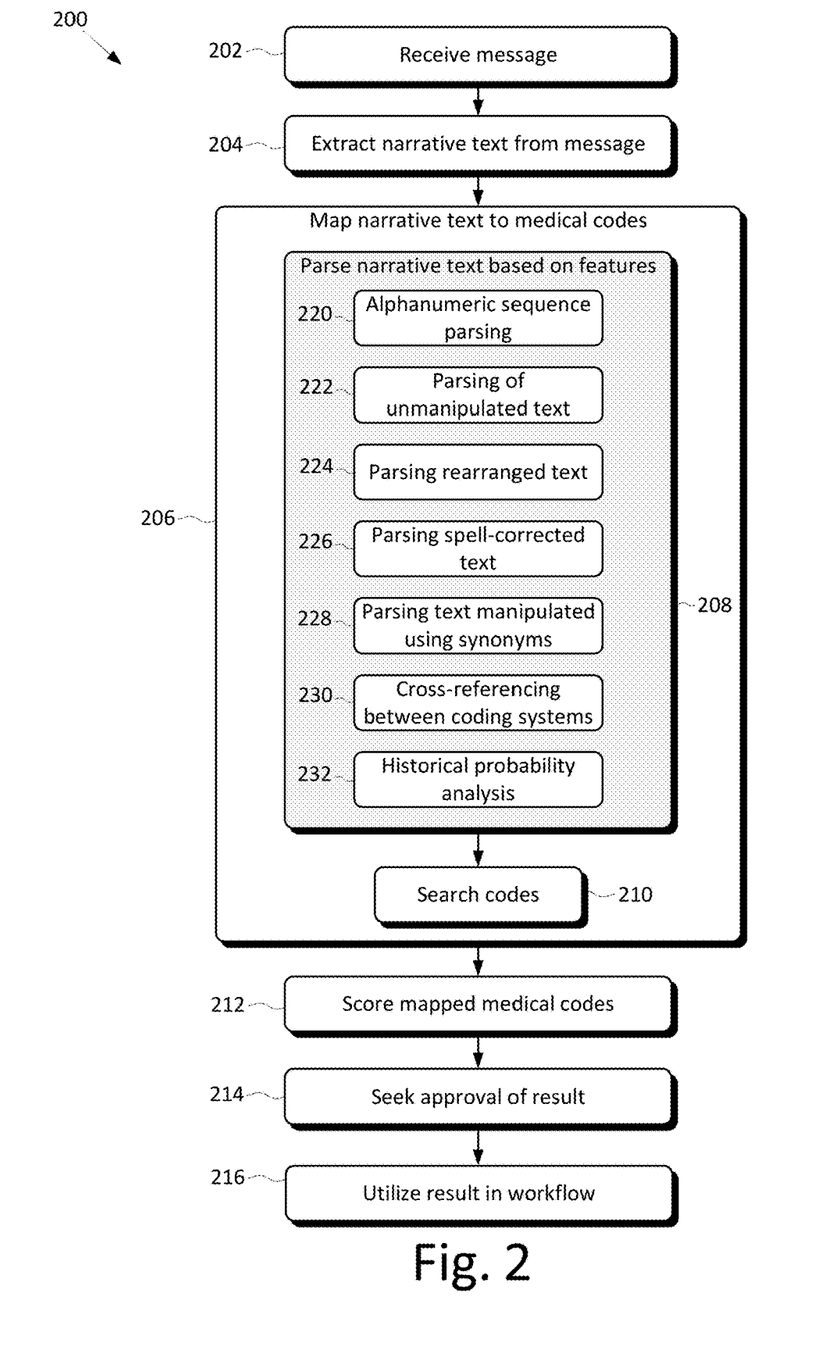
FIG. 2 is a high level flowchart of one embodiment of the method performed by the automatic medical coding system.

FIG. 2 is a high level flowchart of one embodiment of the method performed by the automatic medical coding system 100. The method 200 begins with a message receipt operation 202. The message receipt operation 202 involves the input or transfer of information into the automatic medical coding system 100 via a message containing diagnosis or procedure information. Messages may be generated during routine data entry that involves the notation or selection of a diagnosis or procedure, for example, when checking-in or admitting a patient to a health care facility or documenting a patient encounter. Messages may also be generated as part of preparing, validating, or submitting an electronic document where medical codes are requested or required. For example, messages may be generated when filling out of notice of admission, an insurance eligibility verification inquiry, a medical necessity inquiry, or a request for reimbursement (i.e., a claim). The messages may be generated manually (e.g., submitting a document using a submit button) or automatically as relevant portions of the document (e.g., form) are completed (e.g., after a field loses focus).

An extraction operation 204 extracts portions of the message which may contain information related to a diagnosis or procedure. For example, the extraction operation 204 may extract the value from free-form text (e.g., note fields). The extraction operation 204 may also extract data from fields specifically intended to contain diagnosis or procedure related information, such as diagnosis or procedure code fields and diagnosis or procedure list fields. Demographic data fields (e.g., name and address fields) and other data fields unlikely to contain relevant information (e.g., insurance fields) are not extracted.

A mapping operation 206 parses and maps the extracted data to one or more medical codes using probabilistic matching. The mapping operation 206 may include a number of different parsing operations 208. Different combinations of the parsing operations described herein may be used to map the extracted data to one or more medical codes. The mapping operation also encompasses a code search operation 210 that searches the parsed information against the medical codes or medical code descriptions, as appropriate, from the medical coding system database 122, and/or against historical information medical codes or medical code descriptions from the history database 120

A scoring operation 212 determines one or more of the most probable medical codes from the available alternatives determined through the mapping operation 206 as potential medical codes to be used as the mapped code(s) for each diagnosis or procedure in the extracted data. The score provides a confidence value or other reliability indicator for the mapped medical codes. The results of the various parsing operations for each unique instance of a diagnosis or procedure found in the extracted data may be combined and ranked. The scoring operation 212 may output the highest ranking mapped code for each unique diagnosis or procedure. Where a single mapped medical code is desired or required, a compiled list of competing alternatives for each unique diagnosis or procedure, or a ranked list of competing alternatives for each unique diagnosis or procedure may be provided. For example, only one mapped medical code per diagnosis or procedure is needed if the outcome is intended to be used in a workflow without approval. Alternative medical codes that are not included in the output may be discarded or may be stored for future use if the submitted medical code is rejected. If the automatically mapped medical codes are subject to approval prior to use, the output may be a ranked list of alternative medical codes, optionally showing the scores of each entry on the list.

The output may also include additional information relating to the mapped medical code(s). For example, the scores for each mapped code may optionally be provided in the output. Similarly, the portion of the extracted data that was analyzed and/or the specific strings, words, or phrases parsed may be presented with the corresponding medical codes. The strings, words, or phrases parsed may include the string as originally submitted to the automatic medical coding system 100 and/or as manipulated by the parsing operations.

In an optional approval operation 214, the scored result may be returned to the requesting system for review and approval before the scored result is used. The automatically mapped medical codes may optionally be sent to the provider information system 102 where they are presented to the user, together with information used to determine the medical codes, for approval. The reviewer may approve the mapped medical code, enter a different medical code, or, if alternative medical codes are presented, select one of the alternatives. In some instances, the reviewer may reject the medical code(s) without providing a different code, which may be treated as a request to retry mapping the diagnosis or procedure information excluding the rejected medical code(s).

A result application operation 216 applies the scored result based on the request that initiated the method. For example, the scored result may be used to update information in the requesting system or to complete a document for submission (e.g., to a claim processing system 104).

As previously mentioned, the mapping operation 206 involves the use of one or more parsing operations 208, alone or in various combinations. To the extent that any parsing operation or group of parsing operations are independent, they may generally be performed in any order relative to other parsing operations or groups thereof.

One parsing operation 208 is an alphanumeric sequence parsing operation 220 to locate medical codes that appear within free-form text. The alphanumeric sequence parsing operation 220 searches the extracted data for alphanumeric sequences that are formatted like a medical code and compares the alphanumeric sequence to a set of medicals codes from one or more medical codes systems. The alphanumeric sequence parsing operation 220 may use regular expressions or other pattern matching techniques to locate alphanumeric sequences within the extracted data. For example, alphanumeric sequences starting with a number and having three digits or up to five digits with a decimal point after the third digit may be searched against ICD-9-CM codes. Alphanumeric sequences starting with a letter and having three digits or up to seven digits with a decimal point after the third digit may be searched against ICD-10-CM codes. Alphanumeric sequences having five digits without a decimal point may be searched against CPT® codes. Other sequences corresponding to other medical coding systems may also be parsed for. If the alphanumeric sequence matches a code in the corresponding medical code system, the matching medical code is mapped to the extracted data.

A matching alphanumeric sequence may be used to validate or be validated by medical codes determined using other parsing operations. Similarly, a partial medical code may be completed (i.e., updated to a more specific code) based on the description. For example, the alphanumeric sequence of "274" (ICD-9-CM: "gouty arthropathy, unspecified") appearing in the extracted data, might be confirmed by words describing arthritis appearing in the extracted data. If the extracted data also mentions "acute," the medical code may be enhanced as 274.01 ("acute gouty arthropathy"). If extracted data mentions "chronic," the medical code may be enhanced as 274.02 or 274.03 ("chronic gouty arthropathy with tophus (tophi)") depending on whether a tophus is indicated.

Another parsing operation 208 is a string parsing operation 222 that looks for medical terminology appearing within free-form text. The medical terminology may be derived from the medical code descriptions in the various medical coding systems recognized by the automatic medical coding system 100. When multiple medical coding systems are recognized, there will be some overlapping terminology and potentially some differences in terminology between the different medical coding systems. Accordingly, in some embodiments, the medical terminology from multiple medical coding systems may be aggregated into a single comprehensive medical terminology collection. Searching the extracted data for words and phrases of interest may be simplified by using a comprehensive medical terminology collection, albeit with a potential loss of efficiency when attempting to match words and phrases of interest that do not appear in a particular medical coding system. In contrast, using a separate medical terminology collection for each medical coding system potentially results in inefficiency due to redundant searches, but the words and phrases of interest are expected to appear in at least one of the medical terminology collections' medical code descriptions.

The string parsing operation 222 may be accomplished in a number of different ways. Embodiments may employ a hierarchical set of rules to look for words and phrases of interest. Rules at the top of the hierarchy may search for high frequency words and phrases of interest. When a high frequency word or phrase of interest is found, the rules lower in the hierarchy may search for words that differentiate between medical code descriptions until a uniquely matching medical code description is found or all rules have been exhausted. Other embodiments may employ an iterative process where words or phrases of interest are successively compared to medical code descriptions until a high probability match is found. Still other embodiments may employ queries or filters against data sets.

The string parsing operation 222 may occur in either direction or both directions. Words or phrases of interest found in the extracted data may be compared to medical code descriptions, words or phrases from a medical code description may be compared to the extracted data, or a combination of these techniques may be used. In an example of a one directional search, when a word or phrase of interest (e.g., "arm") appears in a significant number of code descriptions, the string parsing operation 222 may locate additional words or phrases of interest in the extracted data to refine a comparison, query, or filter. In other words, the string parsing operation 222 uses conjunctions to narrow the results. For example, searching medical code descriptions for "arm" and "fracture" produces fewer potential matches. The same process can occur in reverse, searching for words and phrases from the medical code description in the extracted data. In an example of a bi-directional search, when the word "arm" is found in the extracted data, all medical code descriptions containing the word "arm" may be retrieved from the medical coding system data. Next, the string parsing operation 222 may search the extracted data for words appearing in the retrieved medical code descriptions to identify the best match or matches between the extracted data and the medical code descriptions.

The best match may be determined based on a variety of criteria. Suitable criteria include, but are not limited to, exact matches, the number of matching words, the percentage of matching words, the significance of the matching words (e.g., a word like "postdysenteric" being more significant than "left"), the symmetry of the phrasings, the arrangement of the words, and the distance (i.e., the number of interposing words) between the matching words (e.g., "upper part of arm" being a better match to "upper arm" than the words "upper" and "arm" separated by more than a few of words). Multiple criteria may be evaluated to determine the best score. The various criteria may be weighted to increase or reduce the significance of certain criteria in the outcome. The score may represent a confidence value for the result.

The string parsing operation 222 may attempt to match the entire string, or at least all relevant words in the extracted data as a single match. If a match is not found, the string parsing operation 222 may attempt to break the string down into separate elements based on grammatical or proximity features or signals. For example and without limitation, the string parsing operation 222 may attempt to match the extracted data with a medical code description on a sentence by sentence basis or require words to be within a certain number of words to be considered as being associated. One outcome of parsing the string based on grammatical signals is the identification of more than one unique diagnosis or procedure in the string or separate elements within the string (e.g., sentences, phrases, clauses, members of a list) that potentially represent unique diagnoses or procedures.

The basic embodiment of the string parsing operation 222 performs little to no manipulation of the extracted data. Generally, fewer matches are found using only the string parsing operation 222 due to the wide range of variations that can occur in narrative descriptions of the same diagnosis or procedure by different health care providers. However, any matches found using only the string parsing operation 222 may be afforded greater confidence because no artificial manipulation of the data was involved.

The mapping operation 206 may also include other parsing operations that manipulate the extracted data. Data manipulation parsing operations are typically used when the string parsing operation 222 is unsuccessful in mapping at least one medical code to the extracted data or when the result of the string parsing operation 222 lacks a threshold level of confidence, but are not limited to such uses. Data manipulation parsing operations may also be used even when the string parsing operation 222 produces a result that is considered acceptable to validate the result of the string parsing operation 222 or to look for better results. Many of the data manipulation parsing operations involving data manipulations operate in a similar manner to that described in relation to the string parsing operation 222. The main distinction is that data manipulations are used to alter the values being compared before searching the code sets.

One data manipulation parsing operation is a word rearrangement operation 224 that manipulates the arrangement of words in the extracted data based on semantic signals. An example of a manipulation performed by the word rearrangement operation 224 is, without limitation, expansion of a lists based on punctuation, conjunctions, parts of speech, and/or word categories. For example, the extracted data may contain the text "CT of chest, right arm and leg without contrast" from the health care provider notes. The phrase may encompass anywhere from one to three separate medical codes from a medical coding system. While the individual words may be found in various medical code descriptions, a first pass testing the complete phrase is unlikely to generate an exact match or even a match with a sufficient level of confidence.

In a basic embodiment, the word rearrangement operation 224 may employ brute force parsing of the phrase by trying all combinations of the words (e.g., 511 for the exemplary phrase) and selecting the highest scoring matches. In another basic embodiment, the word rearrangement operation 224 may reduce the number of combinations analyzed to conserve computing resources by applying various rules. One logical rule, for example, is common words that have little-to-no distinguishing significance may be ignored (e.g., "of" and "and"). This reduces the analysis to seven words providing 127 combinations. Grammatical rules may further reduce the combinations by breaking the phrase into elements based on signals, including, but not limited to, punctuation (e.g., commas, semi-colons, colons, periods, tabs, spaces, dashes, etc.), control characters (e.g., line feeds and carriage returns), and parts-of-speech (e.g., nouns, verbs, conjunctions, prepositions, adjectives, and/or adverbs). For example, the prepositional "without" modifies "contrast" and has no independent meaning. Moreover, ignoring words of inclusion, omission, or negation is likely to lead to an incorrect match. Thus, "without contrast" would be treated as a single element reducing the analysis to 63 combinations. Other grammatical rules might recognize the list "chest, right arm and leg" as a single element and the list as the object of the prepositional phrase, which may be used to further used to dictate the way the words are combined.

Some embodiments may employ more sophisticated rules. For example, the word rearrangement operation 224 may determine that "chest," "arm," and "leg" are categorized as terms of locality (e.g., anatomical terms) while "CT" is categorized as a diagnostic or procedural term. The word categorization determinations may be based on information obtained from a source such as the medical terminology database 114 or the spelling dictionary 116. The word rearrangement operation 224 may further determine (e.g., based on a set of rules) that the locality terms appear in what may be assumed to be list based on the placement of list separators (e.g., commas and conjunctions) and that the list appears to be an object of a diagnostic or procedural term based on a linking word or phrase (in this case, the preposition "of"). Accordingly, the word rearrangement operation 224 may expand the list by searching each locality term in combination with the diagnostic or procedural term as separate phrases (i.e., "CT chest," "CT right arm", and "CT leg"). In other embodiments, the word rearrangement operation 224 may expand lists and search combinations based solely on grammatical features without recognition of the category of the words. Assuming that the medical coding system contains separate entries for each of the separate phrases, the word rearrangement operation 224 will map the three corresponding medical codes to the extracted data.

The word rearrangement operation 224 may also expand lists by extrapolating modifiers such as adjectives and adverbs which may potential modify one or more terms in a list. For example, in the previous example, word rearrangement operation 224 may determine that "right" potentially modifies both "arm" and "leg" based on the position of the adjective relative to the two nouns. Accordingly, the phrases searched by the word rearrangement operation 224 may include "CT chest," "CT right arm", and "CT right leg." Conversely, if the phrase appearing in the extracted data was "CT of chest, leg, and right arm without contrast," the rule application may be inconclusive and the word rearrangement operation 224 may not modify "leg" with "right."

The decision to modify the word "leg" with "right" may be the difference between mapping two valid medical codes, such as "CT of right leg" and "CT of unspecified leg." The word rearrangement operation 224 may be adjusted to be conservative or aggressive. For example, the threshold value used to determine whether to manipulate the data may be raised or lowered or a confidence factor associated with a speculative manipulation may be lower than for the original phrase. Similarly, a weighting factor may be used to give preference to the more specific or less specific medical code. Even when speculative, the manipulated phrase may produce a better result. For example, if the only possible matches are "CT of right leg" and "CT of left leg" (i.e., "CT of leg" or "CT of unspecified leg" is not an option), comparing "CT of leg" would be inconclusive.

The word rearrangement operation 224 is further capable of handling multiple expansions. For example, expansion of the modifier "without contrast" may be handled in a similar manner to that previously described resulting in the phrases "CT of chest without contrast," "CT of right arm without contrast", and "CT of leg without contrast" being compared, in lieu of or in addition to "CT chest," "CT right arm", "CT leg," "CT right leg," and "CT right leg without contrast."

Another sub-operation is a spell check operation 226 that automatically corrects potentially misspelled words appearing in the extracted data. Because the spell check operation 226 is unsupervised, some changes made by the spell check operation 226 may not be accurate; particularly where words are badly misspelled or several alternatives exist. However, at the expense of processing cost and time, each correction from a pool of potential corrections may be evaluated, for example, in an iterative process. Further, correcting more than a few words in the extracted data may lead to a large number of combinations. Accordingly, some embodiments may limit the number of potential corrections and/or combinations of corrections that may be evaluated. Once corrected, the spell check operation 226 may attempt to map medical codes to the spell-checked data and/or the spell-checked data may be subjected to further manipulation. The results obtained using the spell-checked data may be scored based on factors including, but not limited to, the number of words corrected to obtain the match and the number of alternatives available (fewer is typically better in both cases).

The spell check operation 226 may also expand abbreviations and/or acronyms. Returning to the previous example, the acronym "CT" may be replaced with "computed tomography" to create additional phrases for comparison. Both the original data using the acronym or abbreviation and the manipulated data using the expanded acronym or abbreviation may be compared to the medical code descriptions. Similarly, spelled-out terms may be reduced to their corresponding abbreviations and/or acronyms.

Similarly, a synonym operation 228 may substitute terminology used in the medical code descriptions for synonymous terms appearing the extracted data. The substituted terminology may be more general or more specific than the term being replaced. Continuing with the previous example, the terms "arm" and "leg" may be replaced with "upper extremity" and "lower extremity," respectively, and "extremity," collectively. The term "CT" may be replaced with general synonyms like "imaging" or "scan"

The spell check operation 226 and the synonym operation 228 may also account for singular or plural words (e.g., "extremity" and "extremities"), verb tenses, and other variations (e.g., "image" and "imaging").

A cross-referencing operation 230 may be used to translate a medical code from one medical coding system to another medical coding system. In an extreme example, ICD-9-CM code 733.82 maps to 2,530 ICD-10-CM codes. Accordingly, embodiments may be configured to attempt to map to the more specific medical coding systems first and translate the more specific medical codes into more general medical codes. Alternatively, if a medical code is determined to have one-to-many translation, additional parsing may be performed at that time to refine the medical code according to the more specific medical coding system. Similarly, a single CPT® code may correspond to many ICD codes because the same procedure/treatment can be used for multiple diagnoses. In some cases, translation may not be possible, particularly between procedure codes and diagnosis codes. For example, there are multiple diagnoses where "arthrocentesis of the left shoulder" would be appropriate. Without further information, a diagnosis code cannot be determined.

A historical probability operation 232 may be used to enhance the mapping operation 206. The historical probability operation 232 stores the results of previous mapping operations. Historical results may be separately maintained for each health care provider and/or aggregated for some or all health care providers. In some embodiments, the frequency with which a mapped medical code appears in the history may be factored into the confidence value score for mapped medical codes. In other words, the confidence in rarely occurring medical codes may be discounted. The historical probability operation 232 may also optimize the results by storing strings with the associated mapped code and looking at frequency of usage of the string and/or the words making up the string. The historical probability operation 232 may also store and take into account any approvals and/or rejections by reviewers. Mapped medical codes with high approval rates may be given greater weight. Considering the similarity of the strings/words in the current extracted data to high frequency strings/words, the approval rates for automatically mapped medical codes, which may also include string/word similarity, facilitates learning commonly used phrases for certain diagnoses or procedures and/or specific phrasings used by particular health care providers. Embodiments may employ reported disease information from a government entity (e.g., the U.S. Center for Disease Control or the Centers for Medicare & Medicaid Services), an organization (e.g., the World Health Organization), or a company (e.g., an insurance company) to obtain medical code frequency information, in addition to or in lieu of personally collected historical information.

Figure 3:
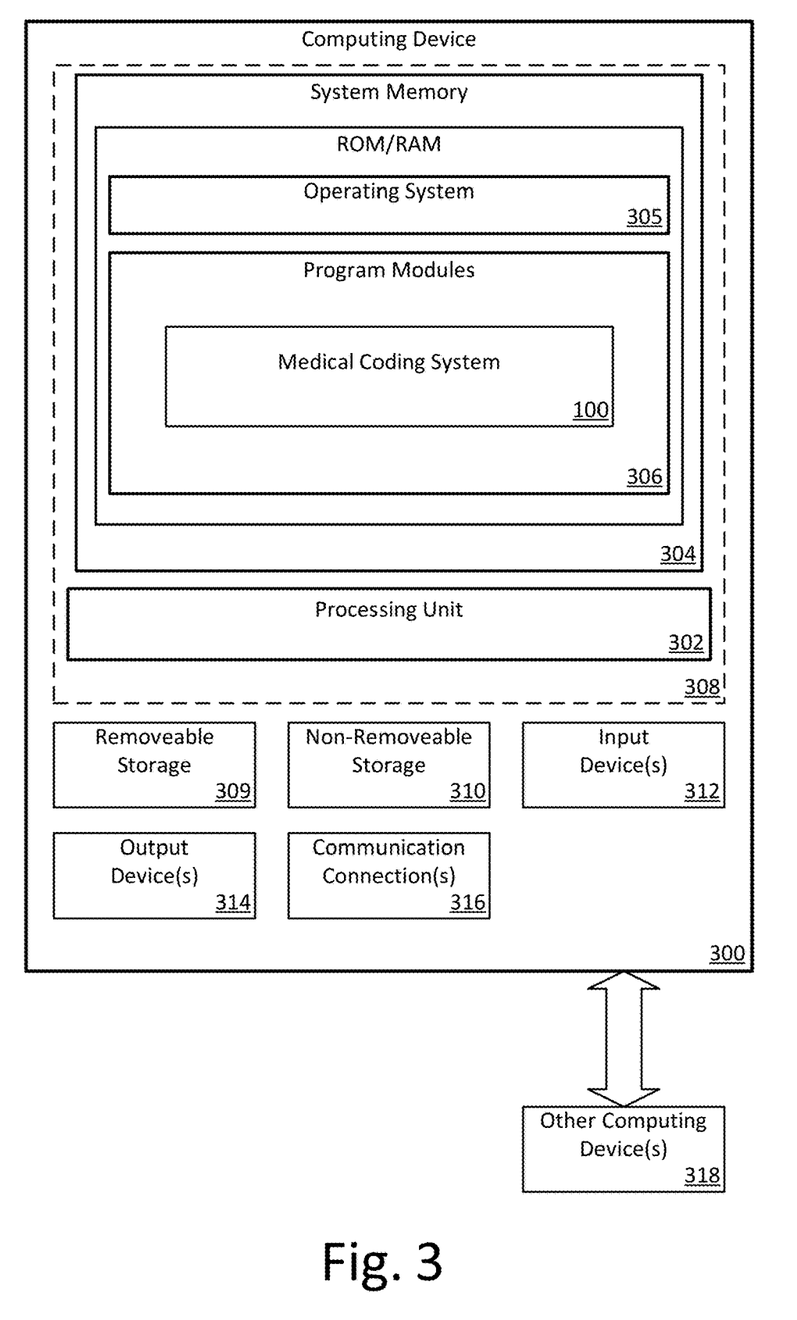
FIG. 3 is a simplified block diagram illustrating example physical components of a computing device with which embodiments of the system may be practiced.

FIG. 3 illustrates one embodiment of a computing device suitable to implement aspects of the disclosure. The computing device 300 may include at least one processing unit 302 and a system memory 304. The system memory 304 may comprise, but is not limited to, volatile (e.g. random access memory (RAM)), non-volatile (e.g. read-only memory (ROM)), flash memory, or any combination. System memory 304 may include operating system 305, one or more programming modules 306, and may include a medical coding system 100 having sufficient computer-executable instructions, which when executed, performs functionalities as described herein. Operating system 305, for example, may be suitable for controlling the operation of computing device 300. Furthermore, aspects of the disclosure may be practiced in conjunction with a graphics library, other operating systems, or any other application program and is not limited to any particular application or system. This basic configuration is illustrated by those components within a dashed line 308. Computing device 300 may also include one or more input device(s) 312 (keyboard, mouse, pen, touch input device, etc.) and one or more output device(s) 314 (e.g., display, speakers, a printer, etc.).

The computing device 300 may also include additional data storage devices (removable and/or non-removable) such as, for example, magnetic disks, optical disks, or tape. Such additional storage is illustrated by a removable storage 309 and a non-removable storage 310. Computing device 300 may also contain a communication connection 316 that may allow device 300 to communicate with other computing devices 318, such as over a network in a distributed computing environment, for example, an intranet or the Internet. Communication connection 316 is one example of communication media.

Program modules, such as the parser 108, the mapper 110, and the scorer 112, may include routines, programs, components, data structures, and other types of structures that may perform particular tasks or that may implement particular abstract data types. Moreover, aspects of the disclosure may be practiced with other computer system configurations, including hand-held devices, multiprocessor systems, microprocessor-based or programmable user electronics, minicomputers, mainframe computers, and the like. Aspects of the disclosure may also be practiced in distributed computing environments where tasks are performed by remote processing devices that are linked through a communications network. In a distributed computing environment, program modules may be located in both local and remote memory storage devices.

Furthermore, aspects of the disclosure may be practiced in an electrical circuit comprising discrete electronic elements, packaged or integrated electronic chips containing logic gates, a circuit utilizing a microprocessor, or on a single chip containing electronic elements or microprocessors. Aspects of the disclosure may also be practiced using other technologies capable of performing logical operations such as, for example, AND, OR, and NOT, including but not limited to mechanical, optical, fluidic, and quantum technologies. In addition, aspects of the disclosure may be practiced within a general purpose computer or in any other circuits or systems.

Aspects of the disclosure, for example, may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, the present disclosure may be embodied in hardware and/or in software (including firmware, resident software, micro-code, etc.). In other words, aspects of the present disclosure may take the form of a computer program product on a computer-usable or computer-readable storage medium having computer-usable or computer-readable program code embodied in the medium for use by or in connection with an instruction execution system.

Although aspects of the present disclosure have been described as being associated with data stored in memory and other storage media, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data and/or computer-executable instructions readable by a computing device. The term "computer-readable storage media" does not include transmission media, such as signals, carrier waves, etc.

Aspects may be utilized in various distributed computing environments where tasks are performed by remote processing devices that are linked through a communications network.

Aspects may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 300 or any other computing devices 318, in combination with computing device 300, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with aspects of the present disclosure.

The description and illustration of one or more aspects provided in this application are intended to provide a complete thorough and complete disclosure the full scope of the subject matter to those skilled in the art and not intended to limit or restrict the scope of the present disclosure as claimed in any way. The aspects, examples, and details provided in this application are considered sufficient to convey possession and enable those skilled in the art to practice the best mode. Descriptions of structures, resources, operations, and acts considered well-known to those skilled in the art may be brief or omitted to avoid obscuring lesser known or unique aspects of the subject matter of this application. The claims should not be construed as being limited to any aspect, example, or detail provided in this application unless expressly stated herein. Regardless of whether shown or described collectively or separately, the various features (both structural and methodological) are intended to be selectively included or omitted to produce an aspect with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept embodied in this application.

What is claimed is:

1. A system for automatically mapping descriptions of diagnoses or procedures to corresponding medical codes from a medical coding system, wherein the medical codes are medical codes having associated diagnosis or procedure descriptions, the system comprising:
   a processor; and
   a memory, including instructions, which when executed by the processor are operable to provide:
   a parser, operable to receive a message comprising diagnosis or procedure information as text in narrative form to extract portions of the message containing the diagnosis or procedure information, wherein the parser manipulates the text according to an amount of manipulation to discover one or more medical code matches associated with the extracted diagnosis or procedure information by:
   correcting spelling of the text;
   substituting synonyms for medical terminology appearing in medical code descriptions in the text with the medical terminology; and
   performing a word arrangement operation within the text based on sematic rules to reduce a number of combinations analyzed to conserve computing resources;
   a mapper, operable to compare un-manipulated text and the manipulated text to the medical code descriptions from the medical coding system to generate a score that corresponds to the amount of manipulation by the parser that results in a match with a given medical code description and when the score meets at least a selected level of confidence, mapping the extracted diagnosis or procedure information to a medical code corresponding to the given medical code description; and
   a scorer, operable to evaluate the score associated with the mapped medical code to determine whether to supply an output including the mapped medical code.

2. A system for automatically mapping descriptions of diagnoses or procedures to corresponding medical codes from a medical coding system, wherein the medical codes are medical codes having associated diagnosis or procedure descriptions, the system comprising:

a medical coding system memory storing medical codes and associated diagnosis or procedure descriptions from the medical coding system;

a processor operable to:

receive a message comprising diagnosis or procedure information;

extract the diagnosis or procedure information from the message;

perform a word arrangement operation within text based on sematic rules to reduce a number of combinations analyzed to conserve computing resources;

automatically map manipulated and/or un-manipulated diagnosis or procedure information to a medical code stored in the medical coding system memory;

score each automatically mapped medical code based in part on the amount of manipulation that results in a match of the medical code stored in the medical coding system memory;

generate a list comprising a selected number of automatically mapped medical codes; and produce an output containing the automatically mapped medical code having a highest score of the automatically mapped medical codes comprising the list.

3. The system of claim 2 further comprising a medical terminology and dictionary memory storing medical terminology appearing in the diagnosis or procedure descriptions of the medical coding system, wherein the processor is further operable to correct the spelling of the diagnosis or procedure information using the medical terminology and dictionary memory.

4. The system of claim 2 further comprising a synonym memory storing synonyms for medical terminology, wherein the processor is further operable to replace terms in the diagnosis or procedure information with synonymous medical terminology using the synonym memory.

5. The system of claim 2 further comprising a history memory for storing historical information relating to a probability that a particular medical code is a most correct medical code for the extracted information.

6. The system of claim 2 wherein the processor is operable to:

locate an alphanumeric sequence within the diagnosis or procedure information having a format matching that used by the medical coding system;

search the medical codes of the medical coding system for the alphanumeric sequence; and if a match is found, map the matching medical code to the diagnosis or procedure information.

7. The system of claim 2 further comprising an index cross-referencing a medical code in one medical coding system to a medical code in another medical coding system, wherein the processor is further operable to translate a first medical code in one medical coding system to a second medical code in another medical coding system.

8. A method of automatically mapping diagnosis or procedure information to corresponding medical codes from a medical coding system, wherein the medical codes have associated diagnosis or procedure descriptions, the method comprising the acts of:

receiving a message comprising diagnosis or procedure information;

extracting the diagnosis or procedure information from the message;

performing a word arrangement operation within text based on sematic rules to reduce a number of combinations analyzed to conserve computing resources;

mapping manipulated and/or un-manipulated diagnosis or procedure information to a medical code from the medical coding system;

scoring each mapped medical code based in part on the amount of manipulation that results in a match of the medical code;

generating a list comprising a selected number of mapped medical codes, wherein the selected number of mapped medical codes are identified to comprise the list based on having higher scores than other mapped medical codes; and supplying an output comprising the mapped medical code according to the score.

9. The method of claim 8 wherein the act of mapping further comprises the acts of:

comparing extracted information to the diagnosis or procedure descriptions from the medical coding system; and if the extracted information matches a diagnosis or procedure description, selecting the medical code associated with the matching diagnosis or procedure description as the mapped medical code.

10. The method of claim 8 wherein the act of mapping further comprises the acts of:

if extracted information does not match a diagnosis or procedure description, manipulating the extracted information;

comparing the manipulated information to the diagnosis or procedure descriptions from the medical coding system; and if the manipulated information matches a diagnosis or procedure description, selecting the medical code associated with the matching diagnosis or procedure description as the mapped medical code.

11. The method of claim 10 wherein the act of manipulating the extracted information further comprises the act of rearranging words from the extracted information.

12. The method of claim 10 wherein the act of manipulating the extracted information further comprises the act of substituting synonyms for words in the extracted information.

13. The method of claim 10 wherein the act of manipulating the extracted information further comprises the act of correcting the spelling of the extracted information.

14. The method of claim 10 wherein the act of manipulating the extracted information further comprises the act of parsing the extracted information based on grammatical signals in the extracted information to separate elements of the extracted information potentially containing descriptions of unique diagnoses or procedures.

15. The method of claim 10 wherein the act of manipulating the extracted information further comprises the act of rearranging elements of the extracted information into differing combinations for comparison with the diagnosis or procedure descriptions.

16. The method of claim 8 wherein the act of mapping further comprises the acts of:

selecting an alphanumeric sequence matching a format followed by the medical codes from the medical coding system;

comparing the selected alphanumeric sequence to the medical codes from the medical coding system; and if the selected alphanumeric sequence matches one of the medical codes, selecting the matching medical code as the mapped medical code.

17. The method of claim 8 wherein the act of scoring the mapped medical code is based on the similarity between elements of the mapped medical code and a corresponding portion of extracted information.

18. The method of claim 8 wherein supplying the output comprising the mapped medical code further comprises supplying the list comprising the selected number of matching medical codes.

19. The method of claim 8 further comprising the act of presenting the mapped medical code to a user for approval before the act of utilizing the mapped medical code.

20. The method of claim 8 further comprising the act of compiling historical information about the mapped medical code corresponding to a portion of extracted information.

* * * * *